United States Patent [19]

Nakanishi

[11] Patent Number: 5,011,408

[45] Date of Patent: Apr. 30, 1991

[54] CHUCK DEVICE FOR DENTAL HANDPIECE

[76] Inventor: Takasuke Nakanishi, c/o Nakanishi Dental Mfg. Co., Ltd., 340 Kamihinata, Kanuma-shi, Tochigi-ken, Japan

[21] Appl. No.: 288,680

[22] Filed: Dec. 22, 1988

[30] Foreign Application Priority Data

Dec. 28, 1987 [JP] Japan ................ 62-329981

[51] Int. Cl.$^5$ .................................. A61C 1/14
[52] U.S. Cl. .................... 433/127; 433/128
[58] Field of Search .............. 433/127, 128, 129; 279/23 R, 41 R, 46 R, 80

[56] References Cited

U.S. PATENT DOCUMENTS

| | | | |
|---|---|---|---|
| 3,051,514 | 8/1962 | Consolloy | 279/41 |
| 3,094,338 | 6/1963 | Page | 279/23 |
| 4,012,841 | 3/1977 | Mosimann | 433/127 |
| 4,370,132 | 1/1983 | Wohlgemuth | 433/128 |
| 4,398,886 | 8/1983 | Schuss et al. | 433/128 |
| 4,436,512 | 3/1984 | Garcia | 433/129 |
| 4,493,645 | 1/1985 | Nakanishi | 433/127 |
| 4,690,641 | 9/1987 | Luiset et al. | 433/129 |

FOREIGN PATENT DOCUMENTS 2015904 9/1979 United Kingdom ............ 279/46 R

Primary Examiner—Robert P. Swiatek
Assistant Examiner—Nicholas D. Lucchesi
Attorney, Agent, or Firm—Malcolm B. Wittenberg

[57] ABSTRACT

A chuck device for a dental handpiece includes a dental bur, a sleeve for accommodating and attaching the dental bur, a push button for detaching the dental bur, and a connecting-removal unit for removably holding and securing the dental bur within the sleeve. The connecting-removal unit includes an elastic engagement member normally engaging with an engaging projection of the dental bur for securing the dental bur within the sleeve, and an opening for accommodating the elastic engagement member within the sleeve or an upper sleeve portion for fitting the elastic engagement member on the outer side of the sleeve. The elastic engagement member has a slit and can be extended apart. When the push button is pushed downwards, the cam surface of the push button abuts on and extends the elastic engagement member apart to release the engagement between the elastic engagement member and the engaging projection of the dental bur to detach the dental bur from the sleeve.

6 Claims, 2 Drawing Sheets

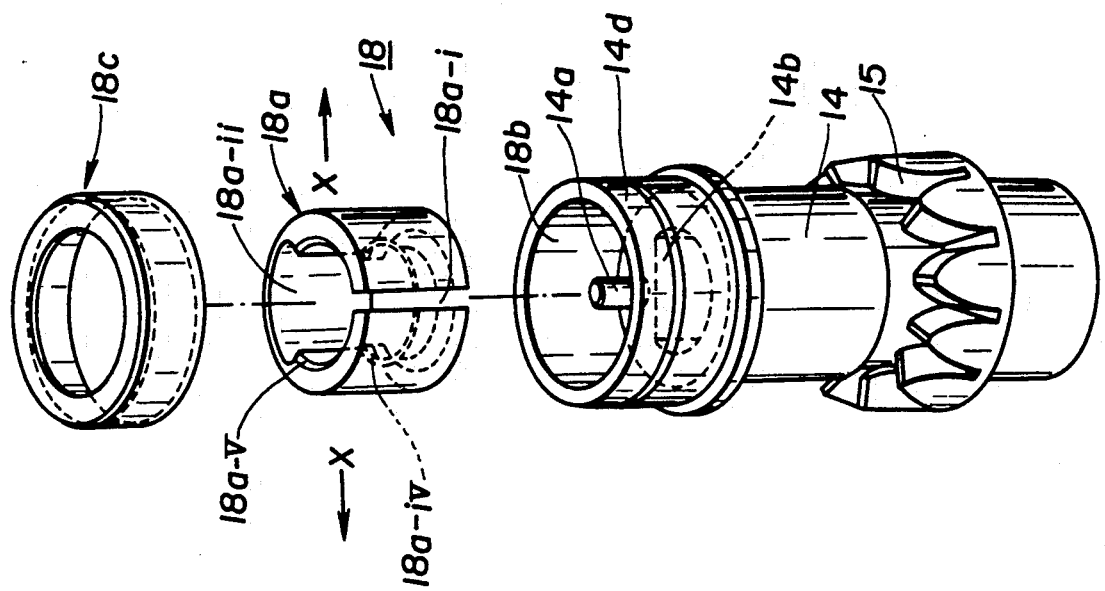
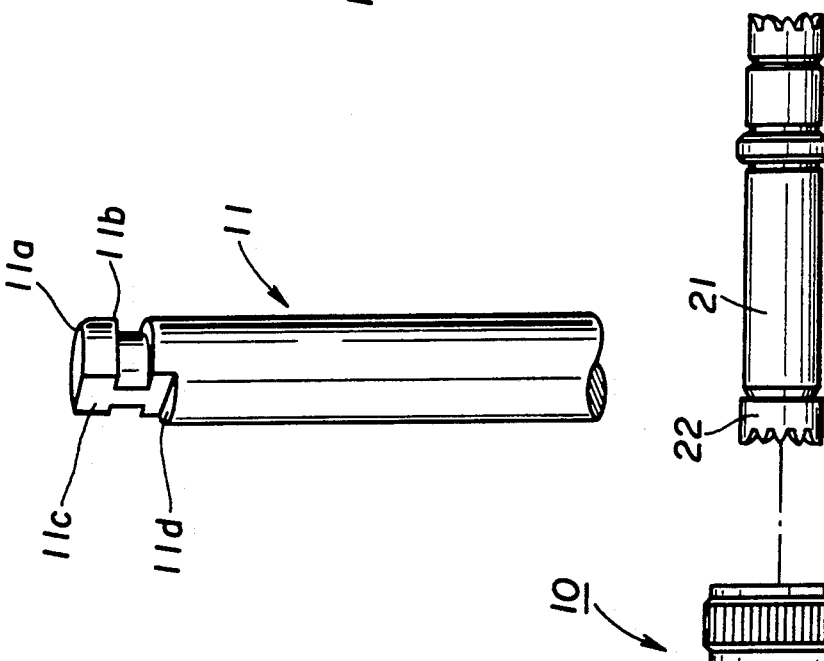
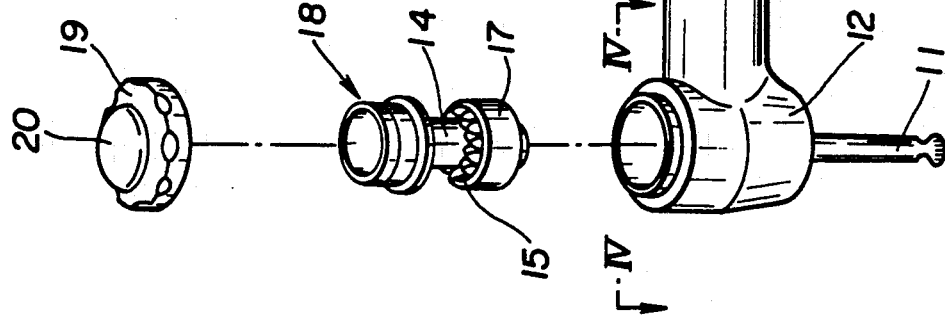

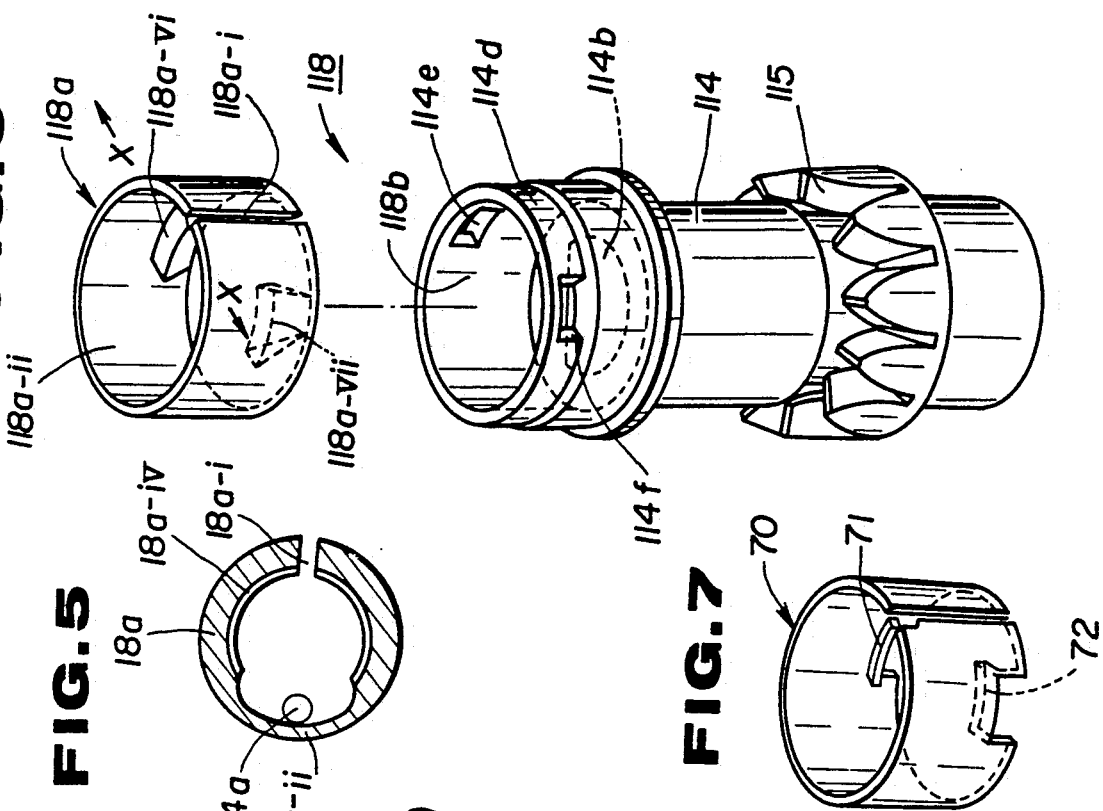
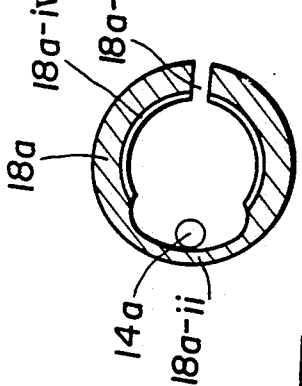
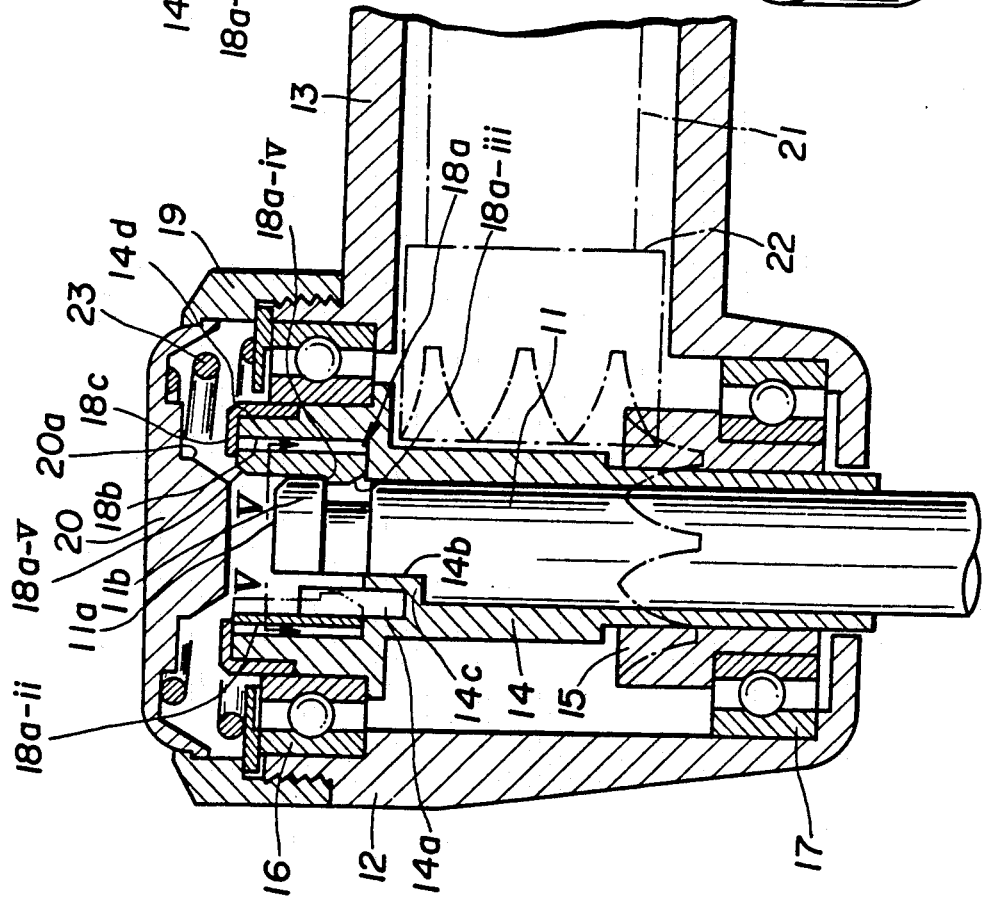

CHUCK DEVICE FOR DENTAL HANDPIECE

BACKGROUND OF THE INVENTION

This invention relates to a chuck device for a dental handpiece.

In the prior art, there are known a variety of chucking devices for a dental handpiece, such as that shown in West German Patent No. 3048061. The chucking device shown in this West German Patent includes a dental bur for dental treatment having a peripheral groove formed in the vicinity of the proximal part thereof, and a head housing sleeve which is provided with a portion engaging with the peripheral groove and which is fitted in the head housing of the dental handpiece. The head housing sleeve may be turned about the longitudinal axis of the handpiece to establish or release the engagement between the peripheral sleeve and the engaging portion to effect connection or detachment of the dental bur. However, this type of the chuck device is not fully satisfactory in making quick exchange of the dental bur since it is necessary to turn the head housing sleeve before proceeding to exchanging the dental bur.

As another type of the chuck device for a dental handpiece, there is known a chuck device wherein the upper end of a sleeve adapted for accommodating and attaching the dental bur is formed with a slit in which a plate spring engaging with the dental bur is mounted, and wherein the arrangement is so made that a cam surface of a push button abuts on the plate spring at the time of exchanging the dental bur to release the engagement between the dental bur and the plate spring. However, with this type of the chuck device, since a groove is formed in the sleeve wall to secure the plate spring to the sleeve for accommodating and attaching the plate spring within the groove, limitations are necessarily imposed on the size of the plate spring and hence that of the engaging surface with the dental bur, so that it is not always possible to provide positive holding and attachment with the dental bur.

SUMMARY OF THE INVENTION

It is a principal object of the present invention to provide a chuck device for a dental handpiece wherein the dental bur can be positively secured simply by being pushed into the device.

It is another object of the present invention to provide a chuck device for a dental handpiece wherein the dental bur can be detached quickly by one-touch operation of pushing the push button.

It is a further object of the present invention to provide a chuck device for a dental handpiece having a structure which is simple but strong and durable against forces acting on the dental bur and which is capable of positively connecting and detaching the dental bur.

These and other objects of the present inention may be accomplished by a chuck device for a dental handpiece comprising a dental tool for applying dental treatment, a sleeve for fitting and securing the dental tool, a push button having a cam surface adapted for detaching the dental tool, and connecting-removal means for positively holding and securing the dental tool within the sleeve and for detaching the dental tool at the time of exchanging the dental tool, the connecting-removal means including an elastic engagement member engaging with an engaging portion of the dental tool for positively holding and securing the dental tool within the sleeve, and attachment means for attaching the elastic engagement member to the sleeve, the elastic engagement member having a slit so that the elastic engagememt member is extended apart about a portion thereof as fulcrum, the engaging portion of the dental tool and the elastic engagement member normally engaging with each other in the non-extended state of the elastic engagement member for positively holding and securing the dental tool within the sleeve, the push button being thrust at the time of exchanging of the dental tool for bringing the cam surface into abutment with the elastic engagement member to extend the elastic engagement member apart to release the engagement between the engagement portion of the dental tool and the elastic engagement member to detach the dental tool from the sleeve.

BRIEF DESCRIPTION OF THE DRAWINGS

FIG.1 is an exploded perspective view showing the foremost part of a dental handpiece having the chuck device of the present invention enclosed therein.

FIG.2 is an exploded perspective view showing an embodiment of a chuck device according to the present invention, with inner parts being also shown in a see-through fashion.

FIG.3 is a fragmentary perspective view showing the upper portion of a dental bur positively held by and secured to the chuck device of the present invention.

FIG.4 is a partial sectional view taken along line IV-IV of FIG.1.

FIG.5 is a sectional view taken along line V-V of FIG.4, with the dental bur being not shown.

FIG.6 is an exploded perspective view similar to FIG.2 showing a modified embodiment of the chuck device of the present invention.

FIG.7 is a perspective view showing a member of the chuck device modified from that shown in FIG.6, with inner parts being shown in a see-through fashion.

PREFERRED EMBODIMENTS OF THE INVENTION

Referring to the drawings, certain preferred embodiments of the present invention will be explained in detail.

Referring first to FIG.1. the foremost part of a dental handpiece is generally shown by a reference numeral 10. The foremost part 10 is formed by a head housing 12 adapted for carrying a dental tool such as a bur 11, and a head housing jacket 13. The head housing 12 houses a bur sleeve 14 for receiving and securing the bur 11, a head gear 15 secured to and adapted for rotating the bur 11, an upper ball bearing 16 (see FIG.4) and a lower ball bearing 17. There is mounted within the bur sleeve 14 a connecting-removal section or unit 18 for holding and securing the bur 11 so that the bur can be connected to and removed from the dental handpiece 10, as later described. A head cap 19 carrying a push button 20 adapted for detaching the bur 11 by one-touch operation is threadedly connected to the top of the head housing 12. There is mounted within the head housing jacket 13 a drive gear 22 which is secured to a rotary shaft 21 connected to and driven into revolutions by a driving electric motor, not shown, and which is brought into meshing with and thereby causing revolutions of the head gear 15.

FIG.2 shows the connecting-removal unit 18 adapted for detachably engaging with and securing the bur 11 at the upper position of the bur sleeve 14. The connecting-removal unit 18 is formed by an elastic engagement member 18a in the form of a split ring adapted to abut on and engage with the bur 11 to secure the bur 11 in position, a bur sleeve opening 18b formed integrally with the bur sleeve 14 and adapted for accommodating and attaching the elastic engagement member 18a, and a detachment inhibit cap 18c overlying the bur sleeve opening 18b for inhibiting detachment of the elastic engagement member 18a upwardly away from the bur sleeve opening 18b. The elastic engagement member 18a is made of synthetic resin, steel or rubber and is in the form of a cylinder having a longitudinal slit 18a-i. The engagememt member 18a is adapted to be extended apart in the direction of arrow marks x, x with a section of the cylinder diametrically opposite to the slit 18a-i as a fulcrum. The outer diameter of the elastic engagement member 18a is selected to be slightly smaller than the inner diameter of the bur sleeve opening 18b, as shown in FIG.4, so that the elastic engagement member 18a may be extended apart radially within the interior of the bur sleeve opening 18b. The inner lower end portion of the elastic engagement member 18a has an inclined cam surface 18a-iii, as shown in FIG.4. The arrangement is so made that, when the bur 11 shown in FIG.3 is introduced into the bur sleeve 14, a head 11a of the bur 11 abuts on the inclined cam surface 18a-iii to extend the elastic engagement member 18a apart radially in the direction of the arrow marks x, x and, as the bur 11 is inserted further, a peripheral engaging projection 11b of the bur 11 is caused to pass by shoulder sections 18a-iv formed at an inner lower portion of the elastic engagement member 18a, the engagement member 18a being then returned to its original unbiased position and the engaging projection 11b then resting on the shoulders 18a-iv for securing the bur 11 within the bur sleeve 14. As shown in FIGS.2, 4 and 5, a holding bar 14a is provided within the bur sleeve opening 18b for securing the elastic engagement member 18a in position between the bar 14a and the inner wall of the bur sleeve 14 so that the elastic engagement member 18a may be prevented from moving to and fro within the bur sleeve opening 18b. The upper portion of the bur 11 is machined to form a facet 11c which is adapted to engage with an abutment surface 14b formed at an upper portion of the bur sleeve 14, see FIG.2, to prevent the bur 11 from being turned about its axis within the bur sleeve 14. The bur sleeve 14 is formed with an abutment step 14c, as shown in FIG.4, which is adapted to engage with shoulder sections 11d of the bur 11 to support force acting on the bur 11. Referring to FIG.4, after the elastic engagement member 18a is positioned within the bur sleeve opening 18b, the detachment inhibit cap 18c is securely fitted to an upper end 14d of the bur sleeve 14 to prevent the elastic engagement member 18a from being detached upwardly away from the bur sleeve opening 18b.

As shown in FIG.4, the push button 20 is fitted to the head cap 19 so as to be normally biased to an upper position shown in FIG.4 by a coil spring 23. The push button 20 has an inclined cam surface 20a and, on pressing the push button 20 downwards, the cam surface 20a abuts on an inclined cam surface 18a-v of the engagement member 18a to extend the elastic engagement member 18a apart to release the engagement between the engaging projection 11b of the bur 11 and the shoulder sections 18a-iv of the elastic engagement member 18a, the bur 11 thus being detached from the bur sleeve 14.

FIG.6 shows a connecting-removal section or unit 118 modified from the unit 18 shown in FIGS.2 and 4. In this figure, the parts or components equivalent to those shown in FIGS.2 and 4 are indicated by the same numerals with numeral 100 being added, and the corresponding description is omitted for simplicity. The connecting-removal section or unit 118 of FIG.6 is formed by an elastic engagement member 118a in the form of a split ring and an upper bur sleeve section 114d formed integrally with the upper portion of a bur sleeve 114 and adapted to be fitted to the elastic engagement member 118a. The connecting-removal unit 118 differs from the unit 18 of FIGS.2 and 4 in that the elastic engagement member 118a is engaged on the outer side of the upper bur sleeve section 114d instead of the inside of a bur sleeve opening 118b. On the inner wall of the elastic engagement member 118a, two shoulder sections 118a-vi, 118a-vii are secured for engaging with the peripheral engaging projection 11b of the bur 11, see FIG.3. These shoulder sections 118a-vi, 118a-vii project into the interior of the bur sleeve opening 118b through through-openings 114e, 114f formed in the bur sleeve 114. The bur 11 may be connected to and removed from the chuck device in the same manner as in the preceding embodiment shown in FIGS.1 to 5. In the connecting-removal unit 118, it is unnecessary to provide the holding bar 14a or the detachment inhibit cap 18c shown in FIG.4.

FIG.7 shows an elastic engagement member 70 in the form of a split ring which is similar to the elastic engagement member 118a shown in FIG.6, except that the shoulder sections 71, 72 are formed integrally with the engagement member by partially cutting and inwardly bending a side wall section of the engagement member 70.

Although the present invention has been described with reference to the preferred embodiments, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A chuck device for a dental handpiece comprising:
a dental tool for applying dental treatment,
a sleeve for fitting and securing said dental tool,
a push button having a cam surface adapted for detaching said dental tool, and
connecting-removal means for positively holding and securing said dental tool within said sleeve and for detaching said dental tool at the time of exchanging said dental tool,
said connecting-removal means including an elastic engagement member engaging with an engaging projection of said dental tool for positively holding and securing said dental tool within said sleeve, and attachment means for attaching said elastic engagement member to said sleeve, said elastic engagement member having a slit so that said elastic engagement member is extended apart about a portion thereof as fulcrum, said elastic engagement member being in the form of a cylinder, the inner surface of which is formed with shoulder sections for engaging and positively holding said engaging projection of said dental tool within the inside of said cylinder, said elastic engagement member being adapted to be extended apart substantially radially within an opening of said sleeve, said engaging projection abutting on and engaging with said shoulder sections for substantially the whole extend of said engaging portion, said engaging projection of said dental tool and said elastic engagement member normally engaging with each other in the non-extended state of said elastic engagement member for positively holding and securing said dental tool within said sleeve, said push button being thrust at the time of exchanging said dental tool for bringing said cam surface into abutment with said elastic engagement member to extend said elastic engagement member apart to release the engagement between said engagement projection of said dental tool and said elastic engagement member to detach said dental tool from said sleeve.

2. The chuck device according to claim 1 wherein a cap is provided overlying said opening of said sleeve to prevent said elastic engagement member from being detached from said opening.

3. The chuck device according to claim 1 wherein a holding member is provided within said opening of said sleeve for preventing said elastic engagement member from moving to and fro within said opening.

4. The chuck device according to claim 2, 3 or 1 wherein said elastic engagement member includes a cam surface at a lower end thereof for abutting on a head portion of said dental tool.

5. The chuck device according to claim 2, 3 or 1 wherein said elastic engagement member includes a cam surface at an upper end thereof for abutting on said cam surface of said push button.

6. A chuck device for a dental handpiece comprising:
a dental tool for applying dental treatment,
a sleeve for fitting and securing said dental tool,
a push button having a cam surface adapted for detaching said dental tool, and
connecting-removal means for positively holding and securing said dental tool within said sleeve and for detaching said dental tool at the time of exchanging said dental tool,
said connecting-removal means including an elastic engagement member engaging with an engaging portion of said dental tool for positively holding and securing said dental tool within said sleeve, and attachment means for attaching said elastic engagement member to said sleeve, said elastic engagement member having a slit so that said elastic engagement member is extended apart about a portion thereof as fulcrum, said elastic engagement member being in the form of a cylinder, the inner side of which is provided with at lest two shoulder sections for positively holding the engaging portion of said dental tool, said elastic engagement member being fitted to an outer side of an outer wall at an upper portion of said sleeve, said shoulder sections projecting into the interior of an opening of said sleeve through through-openings formed in said outer wall, said engaging portion of said dental tool and said elastic engagement member normally engaging with each other in the non-extended state of said elastic engagement member for positively holding and securing said dental tool, said push button being thrust at the time of exchanging said dental tool for bringing said cam surface into abutment with said elastic engagement member to extend said elastic engagement member apart to release the engagement between said engagement portion of said dental tool and said elastic engagement member to detach said dental tool from said sleeve.

* * * * *